US008133452B2

(12) United States Patent
Lee et al.

(10) Patent No.: US 8,133,452 B2

(45) Date of Patent: Mar. 13, 2012

(54) BIOCHIP PACKAGE AND BIOCHIP PACKAGING SUBSTRATE

(75) Inventors: June-Young Lee, Gyeonggi-do (KR); Dong-Ho Lee, Gyeonggi-do (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 772 days.

(21) Appl. No.: 12/179,219

(22) Filed: Jul. 24, 2008

(65) Prior Publication Data

US 2009/0036328 A1 Feb. 5, 2009

(30) Foreign Application Priority Data

Aug. 2, 2007 (KR) ........................ 10-2007-0077766

(51) Int. Cl.

*G01N 21/75* (2006.01)
*C40B 40/04* (2006.01)
*C12M 1/34* (2006.01)

(52) U.S. Cl. ........................ 422/424; 506/15; 435/287.8

(58) Field of Classification Search .................. 422/424; 506/15; 435/287.8

See application file for complete search history.

(56) References Cited

U.S. PATENT DOCUMENTS 6,756,224 B2 6/2004 Vischer
7,736,477 B2 * 6/2010 Nakatani et al. .......... 204/403.01
2002/0177135 A1 * 11/2002 Doung et al. ..................... 435/6
2003/0082587 A1 5/2003 Seul et al.
2003/0113724 A1 6/2003 Schembri et al.
2004/0087033 A1 * 5/2004 Schembri ...................... 436/180
2004/0214312 A1 * 10/2004 Tyvoll et al. ............... 435/288.4
2007/0128069 A1 6/2007 Louis et al.
2007/0259365 A1 11/2007 Hah et al.
2008/0064023 A1 3/2008 Hah et al.

FOREIGN PATENT DOCUMENTS

EP 1471352 A1 10/2004
KR 2005-0037275 4/2005

OTHER PUBLICATIONS

English language abstract of Korea Publication No. 2005-0037275.

* cited by examiner

*Primary Examiner* — Lore Jarrett

(74) *Attorney, Agent, or Firm* — Marger Johnson & McCollom, P.C.

(57) ABSTRACT

A biochip package allowing biochips optimized for high-volume production to be compatible with general-purpose devices and a biochip packaging substrate of the biochip package are provided. The biochip package can include a biochip having a probe array mounted thereon and a biochip packaging substrate on which the biochip is mounted and which has a through cavity exposing a rear surface of the biochip.

24 Claims, 8 Drawing Sheets

BIOCHIP PACKAGE AND BIOCHIP PACKAGING SUBSTRATE

This application claims priority to Korean Patent Application No. 10-2007-0077766, filed Aug. 2, 2007, the disclosure of which is incorporated herein by reference in its entirety.

BACKGROUND

1. Technical Field

The disclosed technology relates to a biochip package and a biochip packaging substrate, and more particularly, to a biochip package allowing biochips optimized for high-volume production to be compatible with general-purpose devices and a biochip packaging substrate of the biochip package.

2. Description of Related Art

Given increased genetics content due to the maturation of the Human Genome Project and development of bioinformatics that can handle enormous amounts of data being generated by large scale projects, there is an increasing need for biochips. The number of biochips that can be formed on a wafer needs to be increased to meet the increasing demand for biochips.

To maximize the number of biochips that are manufactured using one wafer, it is necessary to minimize or remove space not occupied by either a probe array region essential for biochips or regions needed to obtain the accuracy of analysis made by analysis equipment such as a scanner.

Further, there is a need for biochips to have a square n×n format in order to increase the yield of biochips per wafer as well as the productivity of biochip fabrication.

However, analysis equipment such as a fluidics apparatus, a hybridization apparatus, and a scanner are commonly used for the analysis of biochips having a rectangular n×m format. Therefore, there is an urgent need for techniques that enable a square format biochip to be compatible with general-purpose analysis equipment.

SUMMARY

The disclosed technology provides a biochip package that can provide increased yield of biochip fabrication and is compatible with general-purpose analysis equipment.

The disclosed technology also provides a biochip packaging substrate that can provide increased yield of biochip fabrication and is compatible with general-purpose analysis equipment.

Certain embodiments provide a biochip package having a biochip with a probe array mounted thereon, and a biochip packaging substrate on which the biochip is mounted and which has a through cavity exposing a rear surface of the biochip.

BRIEF DESCRIPTION OF THE DRAWINGS

The above and other features and advantages of the disclosed technology will become more apparent by describing in detail various embodiments thereof with reference to the attached drawings in which.

DETAILED DESCRIPTION OF EXAMPLE EMBODIMENTS

Figure 1:
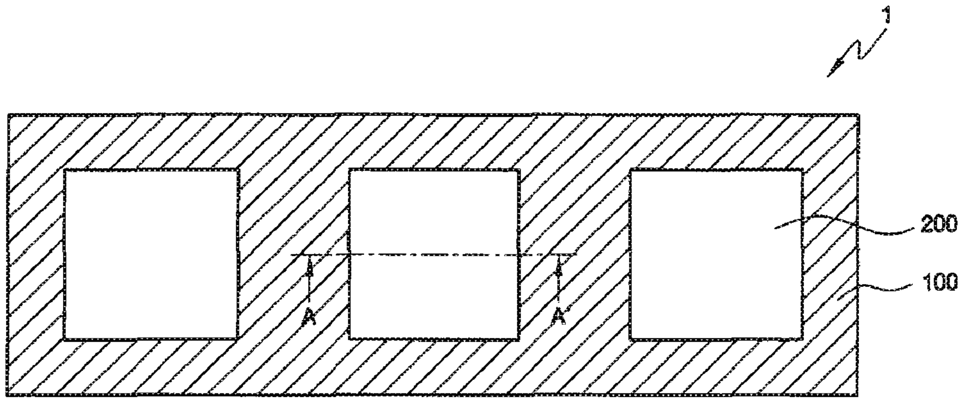
FIG. 1 is a top view of a biochip package according to a first embodiment of the disclosed technology.

Advantages and features of the disclosed technology and methods of accomplishing the same may be understood more readily by reference to the following detailed description of various embodiments and the accompanying drawings. The disclosed technology may, however, be embodied in many different forms and should not be construed as being limited to the embodiments set forth herein. Rather, these embodiments are provided so that this disclosure will be thorough and complete and will fully convey various concepts of the disclosed technology to those skilled in the art, and the present invention will only be defined by the appended claims.

Accordingly, in order to avoid obscuring the invention, in some specific embodiments, well known processing steps, structures, techniques, materials or methods have not been described in detail.

It is noted that the use of any and all examples, or exemplary terms provided herein is intended merely to better illuminate the disclosed technology and is not a limitation on the scope of the invention unless otherwise specified. The use of the terms “a” and “an” and “the” and similar referents in the context of describing the invention (especially in the context of the following claims) are to be construed to cover both the singular and the plural, unless otherwise indicated herein or clearly contradicted by context. As used herein, the singular forms “a”, “an” and “the” are intended to include the plural forms as well, unless the context clearly indicates otherwise. It will be further understood that the terms “comprises” and/or “comprising,” when used in this specification, specify the presence of stated features, integers, steps, operations, elements, and/or components, but do not preclude the presence or addition of one or more other features, integers, steps, operations, elements, components, and/or groups thereof. The terms "comprising," "having," "including," and "containing" are to be construed as open-ended terms (i.e., meaning "including, but not limited to,") unless otherwise noted. As used herein the term "and/or" includes any and all combinations of one or more of the associated listed items.

The disclosed technology will be described with reference to perspective views, cross-sectional views, and/or plan views, in which various embodiments of the disclosed technology are shown. Thus, the profile of an exemplary view may be modified according to manufacturing techniques and/or allowances. That is, the described embodiments of the disclosed technology are not intended to limit the scope of the present invention but cover all changes and modifications that can be caused due to a change in manufacturing process. In the drawings, various components may be exaggerated or reduced for clarity. Like reference numerals refer to like elements throughout the specification.

The disclosed technology will now be described more fully with reference to the accompanying drawings, in which exemplary embodiments are shown.

Biochip packages according to embodiments of the disclosed technology can provide increased yields of biochips per wafer and productivity of biochip fabrication by packaging a biochip with a square (n×n) format into a rectangular (n×m) format so that the biochip is compatible with general-purpose equipment. Further, the disclosed technology provides a novel biochip package that is configured for simple, easy focusing upon analysis using optical equipment, thereby increasing analysis efficiency while achieving compact chip design and high integration.

A biochip package 1 and a biochip packaging substrate 100 of the biochip package 1 according to a first embodiment of the disclosed technology and will now be described in detail with reference to FIGS. 1 through 3.

Figure 2:
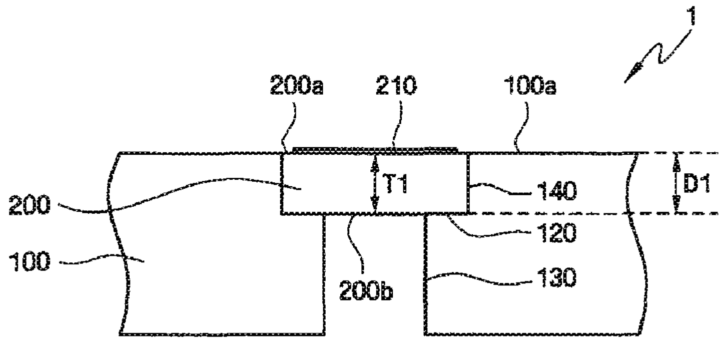
FIG. 2 is a cross-sectional view taken along line A-A' of FIG. 1.
Figure 3:
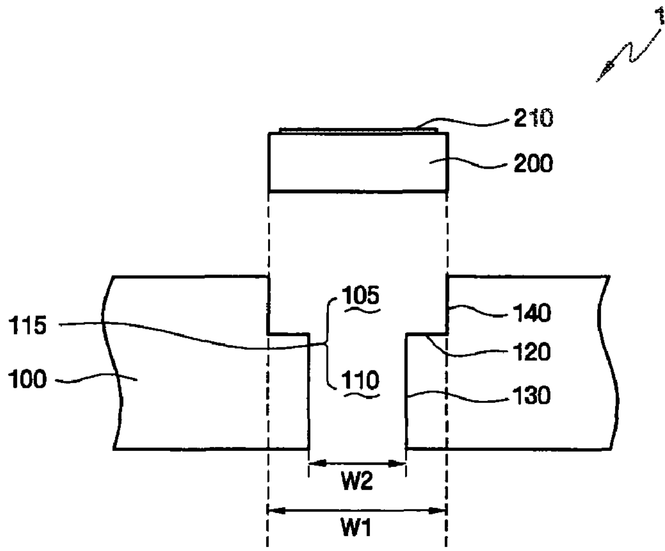
FIG. 3 is an exploded cross-sectional view of a biochip and a biochip packaging substrate in the biochip package of FIG. 1.

FIG. 1 is a top view of a biochip package according to the first embodiment of the disclosed technology, FIG. 2 is a cross-sectional view taken along line A-A' of FIG. 1, and FIG. 3 is an exploded cross-sectional view of a biochip and a biochip packaging substrate in the biochip package of FIG. 1.

Referring to FIGS. 1 through 3, the biochip package 1 includes a biochip packaging substrate 100 and biochips 200 mounted on the biochip packaging substrate 100.

The biochip packaging substrate 100 may have a format or be formed of a material that facilitates adaptation to equipment such as a fluidics apparatus, a hybridization apparatus, and a scanner that are commonly used for the analysis of the biochips 200. The biochip package has a rectangular format, for example, 1 inch by 3 inch, which is suitable for use in commonly used equipment, but the format is not limited thereto.

The biochip packaging substrate 100 may be formed of a polymer material or a plastic material such as polypropylene, polyethylene, polycarbonate, or Acrylonitrile butadiene styrene (ABS), plastic including products sold under the trademarks TEFLON™ and KALREZ™, soda-lime glass, quartz, silicon, or the like.

The biochip 200 used throughout the specification embraces any chip having a square format that is used for gene expression profiling, genotyping, detecting mutations and polymorphisms such as Single Nucleotide Polymorphism (SNP), analysis of proteins and peptides, potential drug screening, development and manufacturing of new drugs, or the like.

A probe array 210 mounted on the biochip 200 may be any probe array manufactured by photolithographic synthesis, ink-jet synthesis, spotting of prefabricated probes, use of beads, or other techniques.

A representative example of probe arrays formed by photolithographic synthesis, which can be effectively applied to the biochip package of the disclosed technology, is described in U.S. patent application Ser. Nos. 11/686,546 and 11/743,477, which have been transferred to the assignee of the present application and are fully incorporated by reference herein.

The biochip packaging substrate 100 includes a through cavity 115 having a mounting portion 105 on which the biochip 200 is mounted and an exposed portion 110. The through cavity 115 has a mounting surface 120 contacting a rear surface **200*b* of the biochip 200, first sidewalls 130 extending from one edge of the mounting surface 120 in a first direction, and second sidewalls 140 extending from the other edge of the mounting surface 120 in a second direction. The width W1 of the mounting surface 105 is greater than the width W2 of the exposed portion 110**.

The biochip 200 is disposed on the mounting portion 105 so as to expose a top surface **200*a* on which the probe array 210 is formed and the rear surface 200*b* through the exposed portion 110. Thus, upon analysis of the biochip 200, a stage for adjusting focusing of a scanner is brought into contact with the rear surface 200*b* of the biochip 200 through the exposed portion 110. The exposed portion 110 may have various cross-sectional shapes including, but not limited to, a quadrangle, polygon, circle, and semi-circle. An adhesive (not shown) may be interposed between the mounting surface 120 and the biochip 200 for attachment and various other techniques may be used to fix the biochip 200**.

In the biochip package 1 according to the present embodiment, the thickness T1 of the biochip 200 may be substantially equal to the depth D1 of the second sidewall 140, so that the top surface **200*a* of the biochip 200 is in the same plane as a top surface 100*a* of the biochip packaging substrate 100. In this case, the biochip 200** has the same planar shape as a conventional chip with a square format.

The biochip package 1 can be used together with a cover slip, hybridization pad and cover, assembled hybridization chamber, or automatic hybridization station.

By using the biochip package 1 having the above-mentioned configuration, analysis efficiency can be significantly improved due to the following reasons.

If a biochip package without an exposed portion 110 is used, a stage for focusing and leveling has to be in contact with the non-planar surface of a biochip packaging substrate 100. This causes the stage to continue to adjust focusing before completing scanning across the entire biochip 200. Further, in spite of continuous focus adjustment, there is a high risk of defocusing.

However, if the biochip package 1 according to the present embodiment is used, a scanner stage for focusing and leveling can be in contact with the highly planar rear surface **200*b* of the biochip 200. Thus, even after one focusing and leveling adjustment, scanning across the entire biochip 200** will not cause defocusing. Thus, the occurrence of errors due to defocusing and the time for analysis of scanning can be reduced and analysis efficiency can be maximized.

Even if a stage for focusing and leveling contacts a biochip instead of a biochip packaging substrate 100, a biochip package without an exposed portion cannot effectively reduce the size of the biochip.

While FIG. 1 illustrates a biochip package 1 having three biochips 200 mounted therein, the number of biochips 200 as well as the integration density of the biochip 200 may vary depending on the usage of the biochip package 1.

Figure 4:
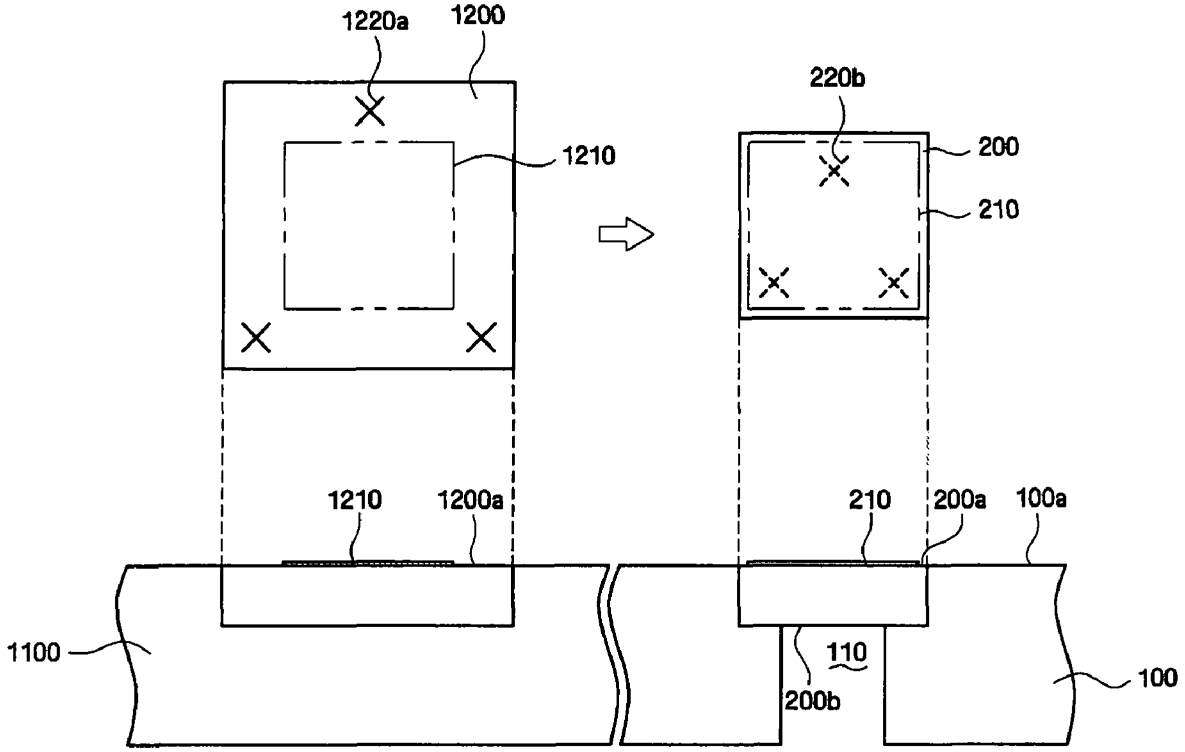
FIG. 4 is a schematic diagram illustrating a biochip packaging substrate with an exposed portion and a biochip packaging substrate without an exposed portion.

FIG. 4 is a schematic diagram illustrating a biochip packaging substrate with an exposed portion and a biochip packaging substrate without an exposed portion, which illustrates a biochip packaging substrate 100 with an exposed portion 110 (right) and a biochip packaging substrate 1100 without the exposed portion 110 (left). For a biochip package without the exposed portion 110, a biochip 1200 must have fixing points 1220*a* for attaching the biochip 1200 defined on a top surface 1200*a* to measure focusing and leveling. Thus, the biochip package requires regions for forming the fixing points 1220*a* in addition to a region for a probe array 1210. However, the biochip 200 in the biochip package according to the present embodiment may have fixing points 220*b* on the rear surface 200*b* of the biochip 200.

That is, the biochip package with the exposed portion 110 eliminates the need to have a region for the fixing points on the top surface 200*a* of the biochip 200, thereby effectively reducing the size of the biochip 200 compared to the biochip package without the exposed portion 110 if both have the same size of the probe array 210. If the biochip 200 has the same size as the biochip 1200, the biochip package with the exposed portion 110 can effectively achieve higher integration density of the probe array 210 on the biochip 200 than the biochip package without the exposed portion 110.

Figure 5:
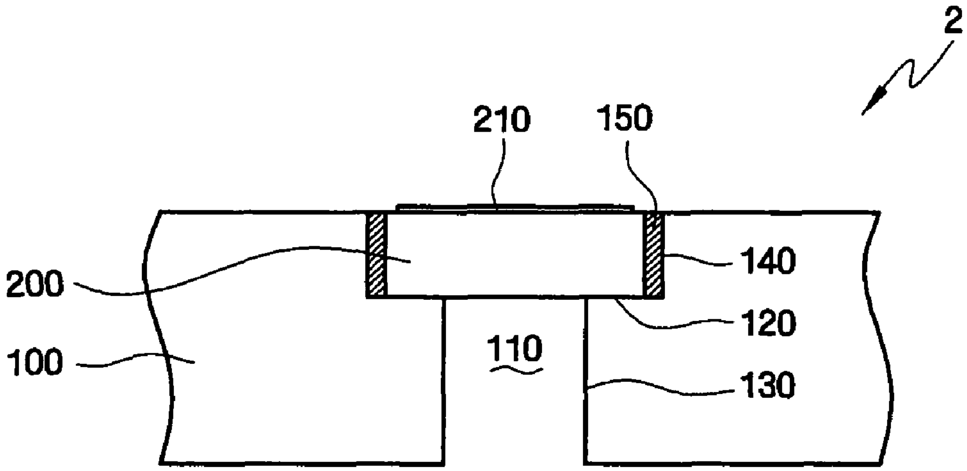
FIG. 5 is a cross-sectional view of a biochip package according to a second embodiment of the disclosed technology.

FIG. 5 is a cross-sectional view of a biochip package 2 according to a second embodiment of the disclosed technology.

Referring to FIG. 5, unlike the biochip package 1, the biochip package 2 according to the present embodiment includes a sealant 150 interposed between a biochip 200 and a second sidewall 140. The sealant 150 serves to more firmly fix the biochip 200 and effectively prevent fluid being used during analysis from leaking through the exposed portion 110.

The sealant 150 may be formed of a material such as silicon or Ecomelt P1 Ex318 (Collano Ebnother A. G. Schweiz), which can be molten upon application of heat and resolidify when cooled or stored at room temperature for a predetermined amount of time. Since the rest of the structure is substantially the same as in the previous embodiment, a detailed explanation thereof will not be given.

Figure 6:
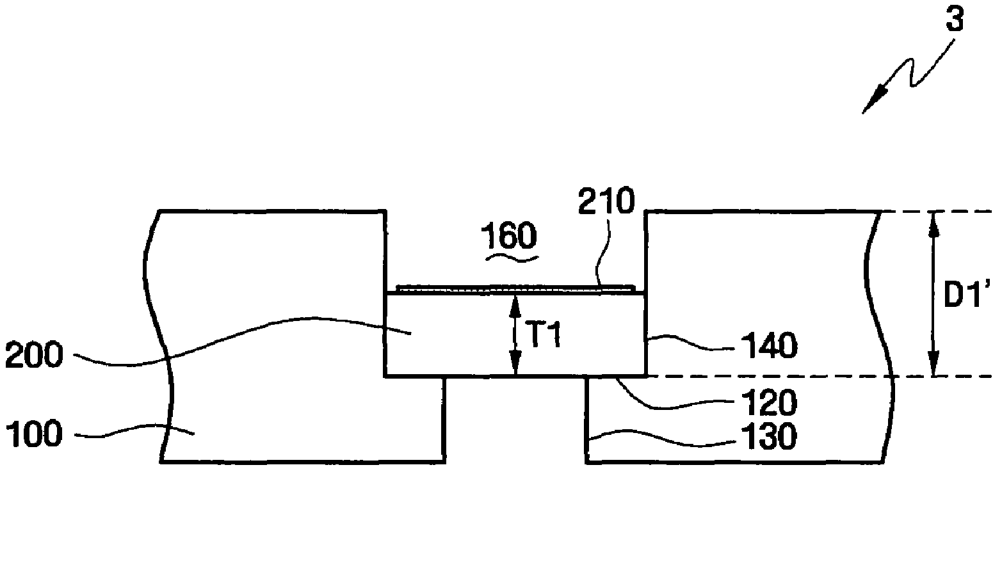
FIG. 6 is a cross-sectional view of a biochip package according to a third embodiment of the disclosed technology.

FIG. 6 is a cross-sectional view of a biochip package 3 according to a third embodiment of the disclosed technology.

Referring to FIG. 6, if the thickness T1 of a biochip 200 is less than the depth D1' of the second sidewall 140, a hybridization reaction space 160 can be provided within the biochip package 3, thereby eliminating the use of an additional hybridization chamber.

Figure 7:
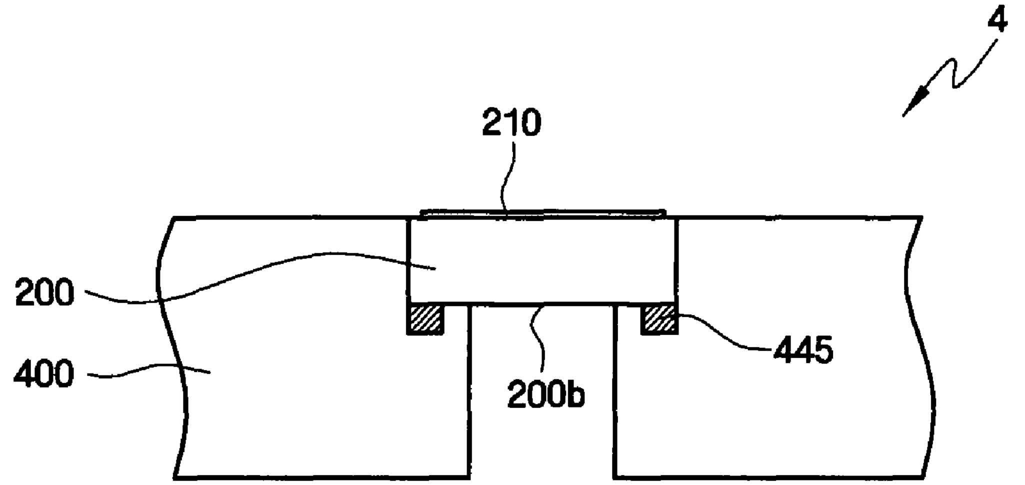
FIG. 7 is a cross-sectional view of a biochip package according to a fourth embodiment of the disclosed technology.
Figure 8:
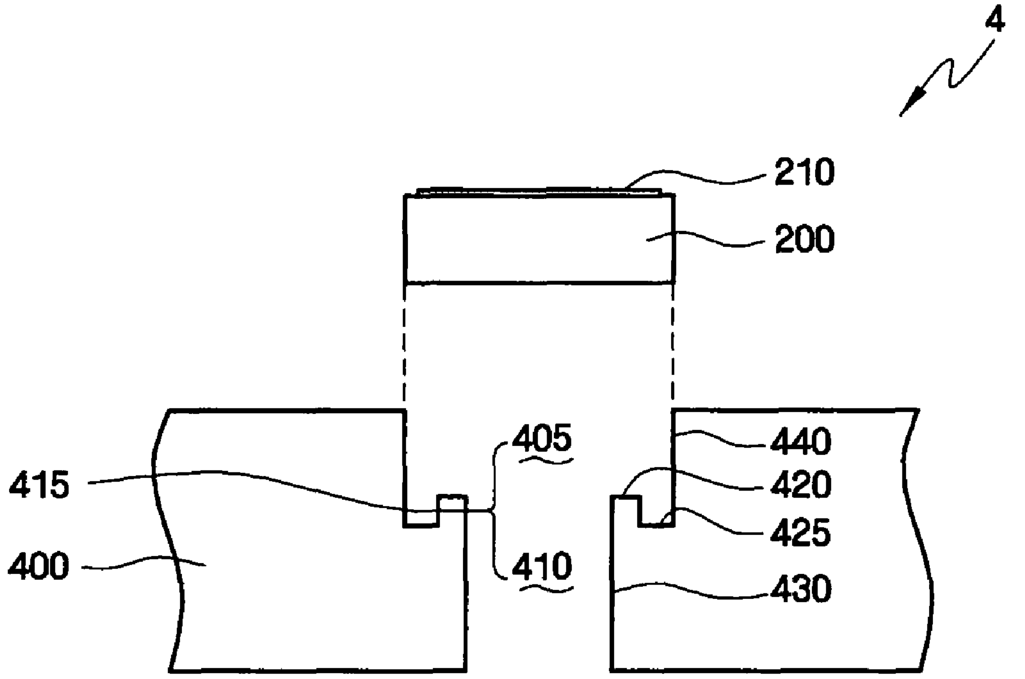
FIG. 8 is an exploded cross-sectional view of a biochip and a biochip packaging substrate in the biochip package of FIG. 7.

FIG. 7 is a cross-sectional view of a biochip package 4 according to a fourth embodiment of the disclosed technology and FIG. 8 is an exploded cross-sectional view of a biochip 200 and a biochip packaging substrate 400 in the biochip package 4.

Referring to FIGS. 7 and 8, a through cavity 415 includes a chip mounting portion 405 and an exposed portion (or an opening) 410. Unlike the through cavity 115 in the biochip package 1, a portion of the chip mounting portion 405 projects out. More specifically, the through cavity 415 has a projecting mounting surface 420 contacting a rear surface 200*b* of the biochip 200, first sidewalls 430 extending from one edge of the mounting surface 420 in a first direction, a recessed surface 425 coupled with the other edge of the mounting surface 420 through another sidewall 423 extending between the mounting surface 420 and the recessed surface 425, and second sidewalls 440 extending from the recessed surface 425 in a second direction opposite the first direction. The through cavity 415 having the above-mentioned construction can increase an adhesion strength between the biochip 200 and the biochip packaging substrate 400 because a larger amount of adhesive 445 can be put into the recessed surface 425. Further, the mounting surface 420 can prevent a fluid being used during analysis from leaking into the exposed portion 410 along a contact surface between the biochip 200 and the biochip packaging substrate 400.

Figure 9:
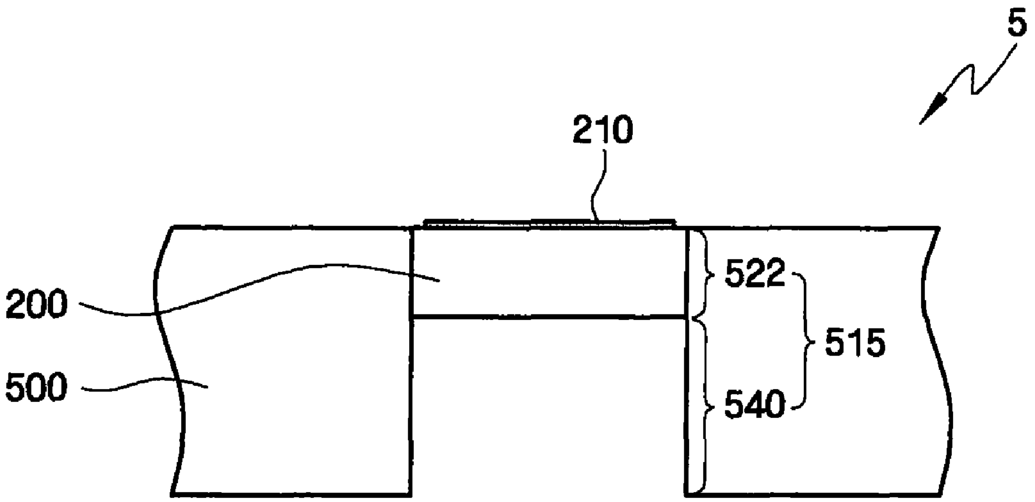
FIG. 9 is a cross-sectional view of a biochip package according to a fifth embodiment of the disclosed technology.
Figure 10:
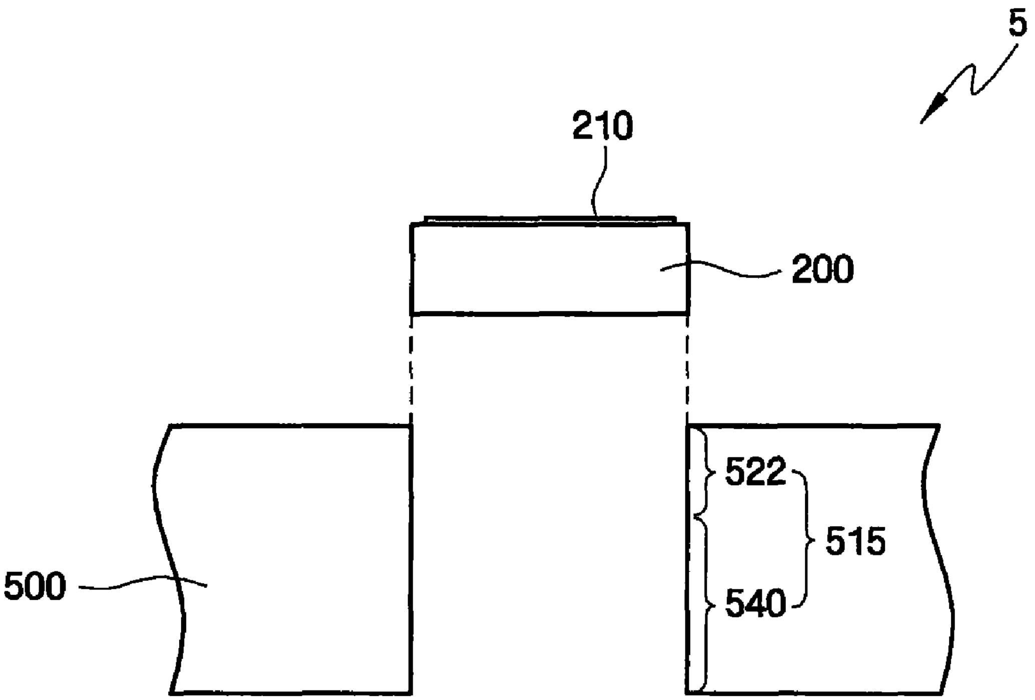
FIG. 10 is an exploded cross-sectional view of a biochip and a biochip packaging substrate in the biochip package of FIG. 9.

FIG. 9 is a cross-sectional view of a biochip package 5 according to a fifth embodiment of the disclosed technology. FIG. 10 is an exploded cross-sectional view of a biochip 200 and a substrate 500 in the biochip package 5.

Referring to FIGS. 9 and 10, a through cavity 515 includes mounting sidewalls 522 contacting sides of the biochip 200 and first sidewalls 540 extending downward from either of the mounting sidewalls 522. The through cavity 515 may further include an adhesive and/or sealant (not shown) provided between the biochip 200 and either of the mounting sidewalls 522.

Figure 11:
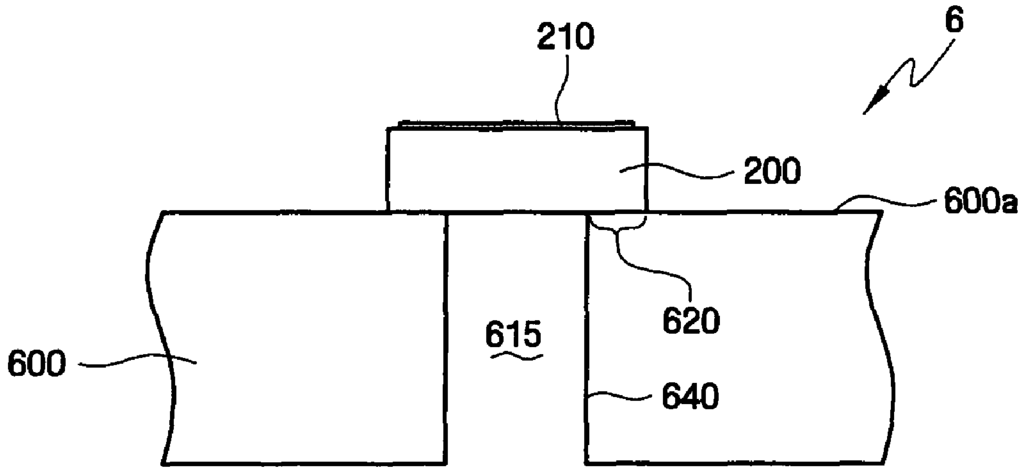
FIG. 11 is a cross-sectional view of a biochip package according to a sixth embodiment of the disclosed technology.
Figure 12:
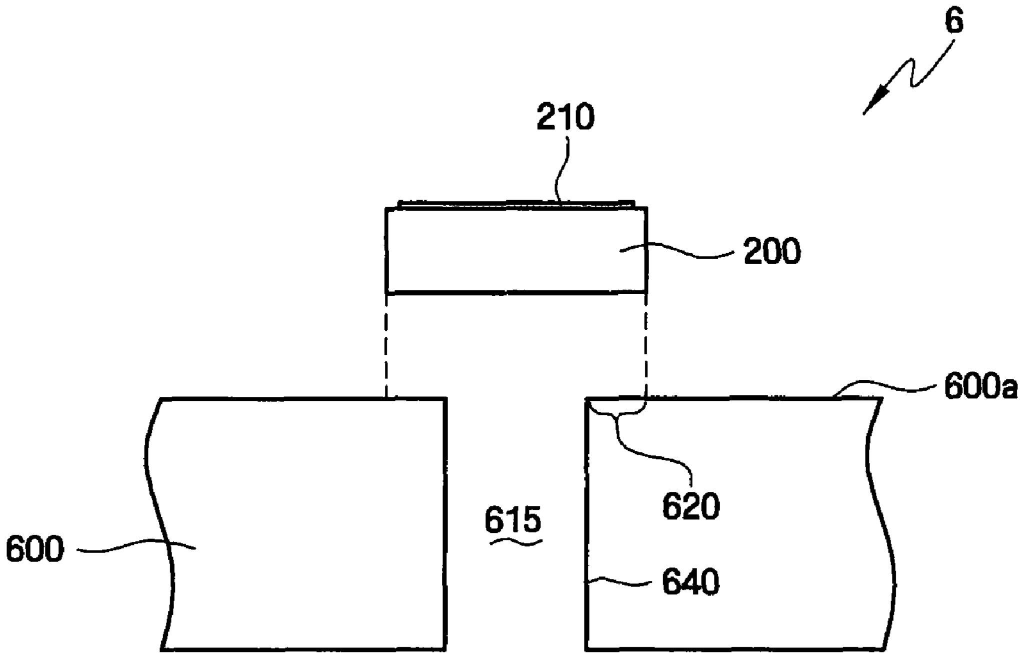
FIG. 12 is an exploded cross-sectional view of a biochip and a biochip packaging substrate in the biochip package of FIG. 11.

FIG. 11 is a cross-sectional view of a biochip package 6 according to a sixth embodiment of the disclosed technology. FIG. 12 is an exploded cross-sectional view of a biochip 200 and a substrate 600 in the biochip package 6.

Referring to FIGS. 11 and 12, the biochip 200 is mounted on a mounting surface 620 that is a portion of a top surface 600*a* of the biochip packaging substrate 600. A through cavity 615 penetrates the substrate 600 and has first sidewalls 640 extending from the mounting surface 620 in a first direction.

Figure 13:
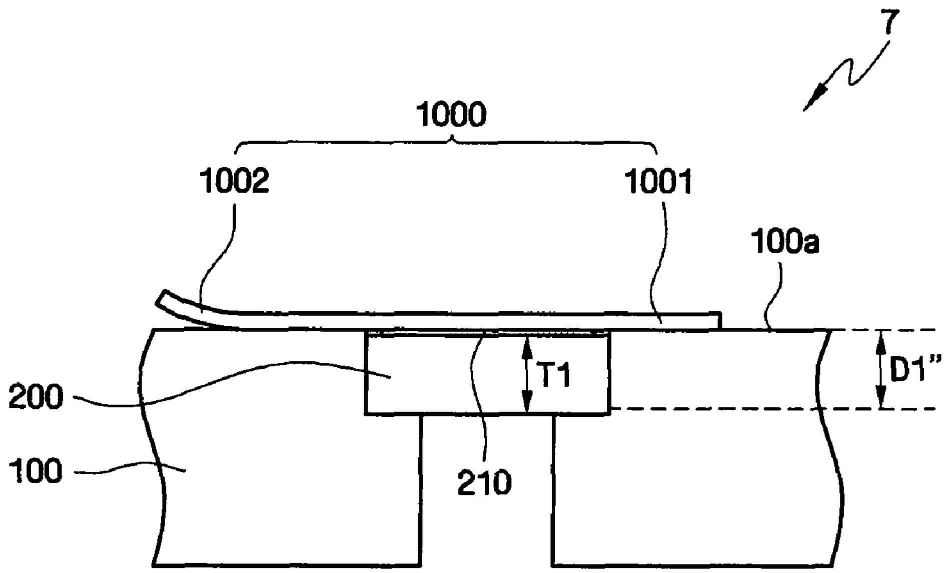
FIG. 13 is a cross-sectional view of a biochip package according to a seventh embodiment of the disclosed technology.

FIG. 13 is a cross-sectional view of a biochip package 7 according to a seventh embodiment of the disclosed technology.

Referring to FIG. 13, the biochip package 7 includes a cover 1000 protecting a probe array 210. Because one end 1001 of the cover 1000 is attached to a top surface 100*a* of a biochip packaging substrate 100 but the other end 1002 is left detached from the biochip packaging substrate 100, the other end 1002 may be lifted up to remove the cover 1000. In order to prevent the cover 1000 from directly contacting the probe array 210, a depth D1" of a chip mounting portion (e.g., the mounting portion 105 of FIG. 3) may be greater than a thickness T1 of the biochip 200. While FIG. 13 shows the cover 1000 is directly attached to the top surface 100*a* of the biochip packaging substrate 100, it may be fixed, if necessary, to a pad (not shown) that is provided on a predetermined region of the top surface 100*a*. If the pad is higher than the probe array 210, the depth D1" of the chip mounting portion may be substantially equal to the thickness T1 of the biochip 200.

Figure 14:
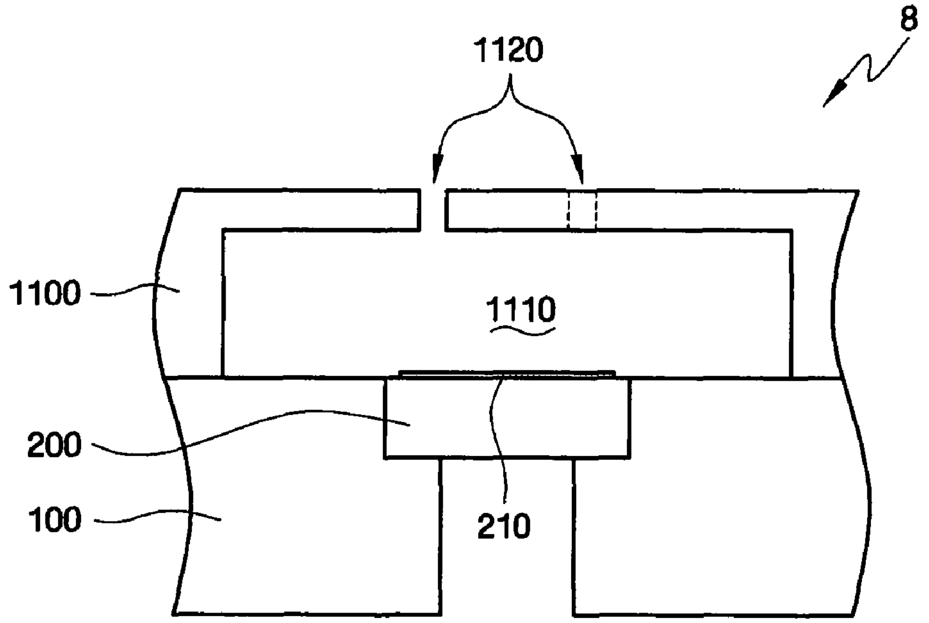
FIG. 14 is a cross-sectional view of a biochip package according to an eighth embodiment of the disclosed technology.

FIG. 14 is a cross-sectional view of a biochip package 8 according to an eighth embodiment of the disclosed technology.

Referring to FIG. 14, the biochip package 8 includes a cover 1100 protecting a probe array 210 and providing a hybridization reaction space 1110. A fluid such as a biosample, cleaning solution, or nitrogen gas may flow into or out of the reaction space 1110 via an inlet/outlet port 1120 penetrating the cover 1100. If the cover 1100 has one inlet/outlet port 1120, the inlet/outlet port 1120 may be responsible for the supply/discharge of fluid. If the cover 1100 has two or more inlet/outlet ports 1120, at least one of the inlet/outlet ports 1120 is responsible for supplying a fluid and at least another one of the inlet/outlet ports 1120 is responsible for discharging a fluid. The inlet/outlet port 1120 may be provided at an external fluid supply tube and/or fluid discharge tube. Although FIG. 14 shows two inlet/outlet ports 1120 that are located at different positions, the number of locations of the inlet/outlet ports 1120 may vary depending on the type of application. The cover 1100 may be bonded to the packaging substrate 100 by anodic bonding or using an adhesive, or mounted thereto via a clamp. The cover 1100 may be combined with the packaging substrate 100 in various other manners.

The cover 1100 is sufficiently high so that a hybridization reaction can occur between the biochip 200 and a bio-sample. For example, the cover 1100 has a height of about 0.1 um. The reaction space 1110 has a width equal to or greater than the width of the biochip 200. More specifically, the reaction space 1110 may have a width just sufficient to surround two edges of the biochip 200 plus margins of about 0.5 cm to about 1.5 cm that allow for smooth hybridization.

Although not shown, the inlet/outlet port 1120 may further include a septum, a plug, and a gasket to keep the reaction space 1110 clean and control reaction conditions.

Figure 15A:
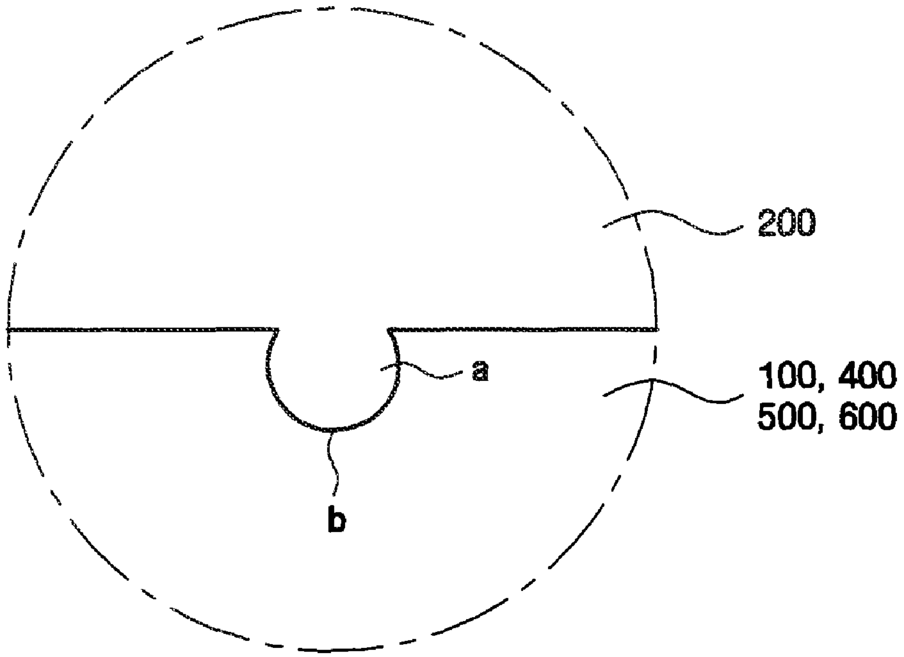
FIGS. 15A and 15B illustrate a boss/recess engagement structure between a biochip and a biochip packaging substrate.
Figure 15B:
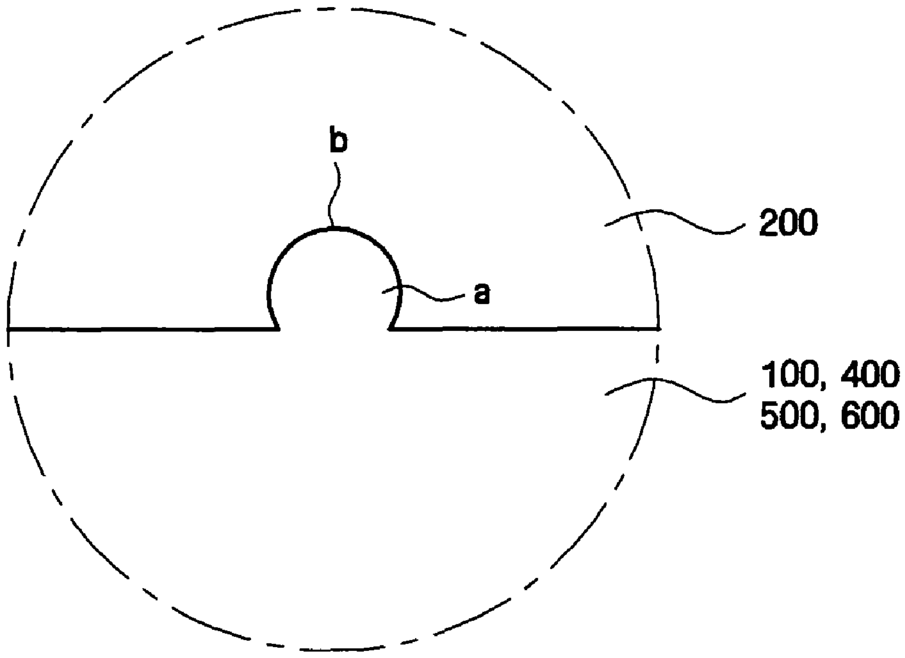

FIGS. 15A and 15B illustrate a boss/recess engagement structure between a biochip 200 and a packaging substrate 100, 400, 500, or 600.

Referring to FIGS. 15A and 15B, one of a boss "a" and a recess "b" is provided for engagement at a contact surface between the biochip 200 and one of the packaging substrates 100, 400, 500, or 600 in, for example, any of the biochip packages 1 through 8 according to the embodiments of the disclosed technology described above with respect to FIGS. 1 through 14. Referring to FIG. 15A, if the boss "a" is provided on a rear surface or sidewall of the biochip 200, the recess "b" may be formed in the packaging substrate 100, 400, 500, or 600. If the recess "b" is formed in the rear surface or sidewall of the biochip 200, the boss "a" is provided on the packaging substrate 100, 400, 500, or 600. The boss/recess engagement allows the biochip 200 to be more firmly mounted to the packaging substrate 100, 400, 500 or 600.

While exemplary embodiments of the disclosed technology have been particularly shown and described with reference to FIGS. 1 through 15B, the individual embodiments may be combined with one another to achieve a new biochip package. For instance, the use of a sealant as in the biochip package 2 of FIG. 5 and the configuration in which the height of a biochip is less than the depth of a second sidewall as in the biochip package 3 of FIG. 6 can be applied, individually or jointly, to another embodiment thereof. Although it is described that the cover 1000 or 1100 is provided on the packaging substrate 100 within the biochip package 7 of FIG. 13 or 8 of FIG. 14, the cover 1000 or 1100 can be applied to the rest of the embodiments.

Biochip packages and substrates mounted therein according to embodiments of the disclosed technology provide improved compatibility of a biochip by packaging a biochip with a square format optimized for high yield and productivity of chips into a rectangular format that is suitable for general-purpose equipment.

The biochip packages according to some embodiments of the disclosed technology are also designed such that a scanner stage for focusing and leveling can contact a highly planar rear surface of a biochip instead of a non-planar surface of a biochip packaging substrate, thereby eliminating the risk of defocusing during scanning across the entire biochip even after one focusing and leveling adjustment.

The biochip packages according to the embodiments of the disclosed technology are also configured so as to define fixing points for a focusing and leveling stage on the rear surface of the biochip, thus eliminating the need to have a region for forming fixing points in addition to a probe array region on the top surface of the biochip. Thus, the disclosed technology can effectively reduce the size of the biochip compared to a biochip package having the same size of a probe array but requiring a region for forming fixing points on a top surface of the biochip. The disclosed technology can also effectively achieve higher integration density of the probe array on the biochip than a biochip package without an exposed portion.

While the present invention has been particularly shown and described with reference to exemplary embodiments thereof, it will be understood by those of ordinary skill in the art that various changes in form and details may be made therein without departing from the spirit and scope of the present invention as defined by the following claims. It is therefore desired that the present embodiments be considered in all respects as illustrative and not restrictive, reference being made to the appended claims to indicate the scope of the invention.

What is claimed is:

1. A biochip package comprising:

a biochip mounted on a biochip packaging substrate, wherein the biochip packaging substrate comprises a through cavity exposing a portion of a rear surface of the biochip; and a probe array mounted on the biochip, wherein the biochip has a top surface on which the probe array is formed, and wherein the top surface is opposite to the rear surface.

2. The biochip package of claim 1, wherein the biochip has a square format and the biochip packaging substrate has a rectangular format.

3. The biochip package of claim 1, wherein a boss/recess engagement is made between the biochip and the biochip packaging substrate.

4. The biochip package of claim 1, wherein the through cavity comprises:

a mounting surface contacting the rear surface of the biochip;

first sidewalls extending from one edge of the mounting surface in a first direction; and second sidewalls extending from the other edge of the mounting surface in a second direction.

5. The biochip package of claim 1, wherein the through cavity comprises:

a projecting mounting surface contacting the rear surface of the biochip;

first sidewalls extending from one edge of the mounting surface in a first direction;

a recessed surface coupled with the other edge of the mounting surface; and second sidewalls extending from the recessed surface in a second direction.

6. The biochip package of claim 4 or 5, wherein a thickness of the biochip is not more than a depth of the second sidewalls.

7. The biochip package of claim 6, further comprising a sealant interposed between the biochip and the second sidewalls.

8. The biochip package of claim 6, further comprising an adhesive deposited on the recessed surface.

9. The biochip package of claim 1, wherein the through cavity comprises:

mounting sidewalls contacting sides of the biochip; and first sidewalls extending downward from the mounting sidewalls.

10. The biochip package of claim 9, further comprising at least one of an adhesive and a sealant provided between the biochip and the mounting sidewalls.

11. The biochip package of claim 1, wherein the biochip is mounted on a mounting surface of the biochip packaging substrate, the through cavity penetrating the biochip packaging substrate, the through cavity having first sidewalls extending from the mounting surface in a first direction.

12. The biochip package of claim 1, wherein the biochip packaging substrate comprises a plurality of through cavities.

13. The biochip package of claim 1, further comprising a cover protecting the probe array.

14. The biochip package of claim 13, wherein the cover cooperates with the biochip packaging substrate to provide a hybridization reaction space.

15. A biochip packaging substrate on which a biochip is mounted and comprising a through cavity exposing a rear surface of the biochip, wherein the biochip has a top surface on which a probe array is formed, and wherein the top surface is opposite to the rear surface.

16. The biochip packaging substrate of claim 15, wherein the biochip has a square format and the biochip packaging substrate has a rectangular format.

17. The biochip packaging substrate of claim 15, further comprising one of a boss and a recess that makes a boss/recess engagement with the biochip.

18. The biochip packaging substrate of claim 15, wherein the through cavity comprises:

- a mounting surface contacting the rear surface of the biochip;
- first sidewalls extending from one edge of the mounting surface in a first direction; and
- second sidewalls extending from the other edge of the mounting surface in a second direction opposite the first direction.

19. The biochip packaging substrate of claim 15, wherein the through cavity comprises:

- a projecting mounting surface contacting the rear surface of the biochip;
- first sidewalls extending from one edge of the mounting surface in a first direction;
- a recessed surface coupled with the other edge of the mounting surface; and
- second sidewalls extending from the recessed surface in a second direction opposite the first direction.

20. The biochip packaging substrate of claim 19, further comprising an adhesive deposited on the recessed surface.

21. The biochip packaging substrate of claim 15, wherein the through cavity comprises:

- mounting sidewalls contacting sides of the biochip; and
- first sidewalls extending downward from the mounting sidewalls.

22. The biochip packaging substrate of claim 15, wherein the biochip is mounted on a mounting surface of the biochip packaging substrate, the through cavity penetrating the biochip packaging substrate, the through cavity having first sidewalls extending from the mounting surface in a first direction.

23. The biochip packaging substrate of claim 15, further comprising a cover.

24. The biochip packaging substrate of claim 23, wherein the cover cooperates with the biochip packaging substrate to provide a hybridization reaction space.

* * * * *